(12) United States Patent
Farruggio et al.

(10) Patent No.: US 12,291,706 B2
(45) Date of Patent: *May 6, 2025

(54) METHODS FOR SCREENING VARIANT OF TARGET GENE

(71) Applicant: APPLIED STEMCELL, INC., Milpitas, CA (US)

(72) Inventors: Alfonso Farruggio, Stanford, CA (US); Ruby Yanru Tsai, San Jose, CA (US); Lingjie Kong, Union City, CA (US)

(73) Assignee: APPLIED STEMCELL, INC., Milpitas, CA (US)

( * ) Notice: Subject to any disclaimer, the term of this patent is extended or adjusted under 35 U.S.C. 154(b) by 1104 days.

This patent is subject to a terminal disclaimer.

(21) Appl. No.: 16/968,602

(22) PCT Filed: Feb. 8, 2019

(86) PCT No.: PCT/US2019/017375
§ 371 (c)(1),
(2) Date: Aug. 9, 2020

(87) PCT Pub. No.: WO2019/157395
PCT Pub. Date: Aug. 15, 2019

(65) Prior Publication Data
US 2020/0385710 A1 Dec. 10, 2020

Related U.S. Application Data

(60) Provisional application No. 62/628,236, filed on Feb. 8, 2018.

(51) Int. Cl.
*C12N 15/85* (2006.01)
*C12N 15/10* (2006.01)
*C12N 15/90* (2006.01)
*C40B 40/04* (2006.01)

(52) U.S. Cl.
CPC ..... *C12N 15/1082* (2013.01); *C12N 15/1034* (2013.01); *C12N 15/907* (2013.01); *C12N 2800/30* (2013.01); *C12N 2830/002* (2013.01); *C12N 2830/003* (2013.01)

(58) Field of Classification Search
None
See application file for complete search history.

(56) References Cited

U.S. PATENT DOCUMENTS

| | | | |
|---|---|---|---|
| 2002/0094516 A1 | 7/2002 | Calos et al. | |
| 2004/0072215 A1 | 4/2004 | Rudi et al. | |
| 2004/0087014 A1 | 5/2004 | Huse | |
| 2005/0089960 A1 | 4/2005 | Wahlberg et al. | |
| 2006/0172377 A1 | 8/2006 | Padidam | |
| 2015/0140665 A1 | 5/2015 | Calos et al. | |
| 2016/0053280 A1 | 2/2016 | Deshpande et al. | |
| 2016/0184394 A1 | 6/2016 | Schaffer et al. | |
| 2017/0193647 A1* | 7/2017 | Huang | G01V 1/28 |
| 2017/0211061 A1 | 7/2017 | Weiss et al. | |
| 2017/0327806 A1 | 11/2017 | Joung et al. | |
| 2018/0319850 A1* | 11/2018 | Payne | C12N 9/22 |

FOREIGN PATENT DOCUMENTS

WO 2017/081288 A1 5/2017
WO 2017/180669 A1 10/2017

OTHER PUBLICATIONS

Annahita Keravala and Michele P. Calos, "Site-Specific Chromosomal Integration Mediated by C31 Integrase", Methods in Molecular Biology, vol. 435: Chromosomal Mutagenesis, pp. 165-173.
Yuan Yu et al., "Improved site-specific recombinase-based method to produce selectable marker- and vector-backbone-free transgenic cells", Scientific Reports, 4:4240 | DOI: 10.1038/srep04240, Feb. 28, 2014, pp. 1-7.
Nuria Vilaboa et al., "Gene Switches for Deliberate Regulation of Transgene Expression: Recent Advances in System Development and Uses", Journal of Genetic Syndromes & Gene Therapy, ISSN:2157-7412, vol. 2, Issue 3, Nov. 11, 2011, pp. 1-23.
Shubhra Gupta, "Codon Optimization", CBS 521, May 5, 2003, pp. 1-13.
X. Duportet et al., "A platform for rapid prototyping of synthetic gene networks in mammalian cells", Nucleic Acids Research, vol. 42, No. 21, Dec. 1, 2014 (Dec. 1, 2014), pp. 13440-13451, XP055359411, GB ISSN: 0305-1048, DOI: 10.1093/nar/gku1082 *the whole document*.
F. Zhu et al., " DICE, an efficient system for iterative genomic editing in human pluripotent stem cells", Nucleic Acids Research, Dec. 4, 2013 (Dec. 4, 2013), XP055106313, ISSN: 0305-1048, DOI: 10.1093/nar/gkt1290 *the whole document*.
Zhengyao Xu et al., "Accuracy and efficiency define Bxb1 integrase as the best of fifteen candidate serine recombinases for the integration of DNA into the human genome", BMC Biotechnology, Biomed Central Ltd, vol. 13, No. 1, Oct. 20, 2013 (Oct. 20, 2013), pp. 1-17, XP021171155, ISSN: 1472-6750, DOI: 10.1186/1472-6750-13-87 *the whole document*.
Sivaprakash Ramalingam et al., "Generation and Genetic Engineering of Human Induced Pluripotent Stem Cells Using Designed Zinc Finger Nucleases", Stem Cells and Development, vol. 22, No. 4, Aug. 30, 2012 (Aug. 30, 2012) , pp. 595-610, XP055265383, US ISSN: 1547-3287, DOI: 10.1089/scd.2012.0245 *the whole document*.

* cited by examiner

*Primary Examiner* — Maria Marvich
(74) *Attorney, Agent, or Firm* — Jun He Law Offices P.C; Yi Zhang

(57) ABSTRACT

Provided are methods for screening a desired variant of a target gene in a eukaryotic system. Compositions for screening a desired variant of a target gene are also provided.

13 Claims, 6 Drawing Sheets

Specification includes a Sequence Listing.

Integration efficiency assay:
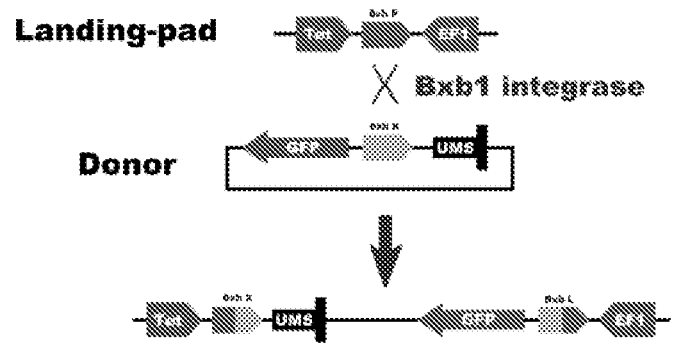
Flow cytometry results:
AAVS1, negative control (0.74%)
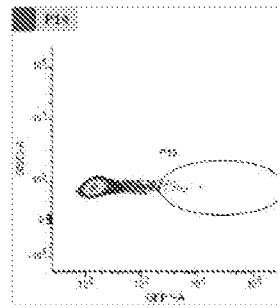
AAVS1 integration (15.4%)
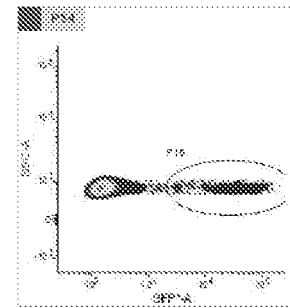
H11, negative control (0.85%)
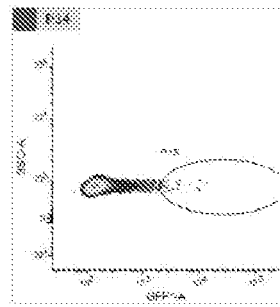
H11 integration (19.4%)
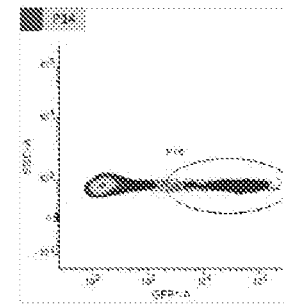
FIG. 1

SEQ ID NO: 1 cgccaccATGGCTAGAGCCCTGGTGGTCATCAGACTGAGCAGAGTGACCGACGCCACCACCTCTCCAG
*Kozak codon-optimized Bxb1* →
AGAGACAGCTGGAAAGCTGCCAGCAGCTGTGTGCCCAGCGAGGCTGGGATGTTGTTGGAGTGGCTGAG

GACCTGGATGTGTCTGGCGCCGTGGATCCCTTCGACAGAAAGAGAAGGCCCAACCTGGCCAGATGGCT

GGCCTTTGAGGAACAGCCCTTCGACGTGATCGTGGCCTACAGAGTGGACCGGCTGACCCGGTCTATCA

GACATCTGCAGCAGCTGGTTCACTGGGCCGAAGATCACAAGAAACTGGTGGTGTCCGCCACAGAGGCC

CACTTCGATACCACCACACCTTTTGCCGCCGTCGTGATCGCCCTGATGGGAACAGTTGCCCAGATGGA

ACTGGAAGCCATCAAGAGCGGAACAGAAGCGCCGCTCACTTCAACATCAGAGCCGGCAAGTACAGAG

GCAGCCTGCCACCTTGGGGCTACCTGCCAACAAGAGTGGATGGCGAATGGCGGCTGGTGCCTGATCCT

GTGCAGCGGGAAAGAATCCTGGAAGTGTACCACAGAGTGGTGGACAACCACGAGCCTCTGCATCTGGT

GGCCCACGACCTGAATAGAAGAGGCGTGCTGAGCCCTAAGGACTACTTCGCCCAACTGCAGGGCAGAG

AGCCTCAGGGAAGAGAGTGGAGCGCTACAGCCCTGAAGCGGAGCATGATCTCTGAGGCCATGCTGGGC

TACGCCACACTGAATGGAAAGACCGTGCGGGACGATGATGGCGCCCCTCTCGTTAGAGCCGAGCCTAT

CCTGACACGCGAGCAGCTGGAAGCCCTGAGAGCCGAACTGGTCAAGACCAGCAGAGCCAAGCCTGCCG

TGTCTACACCTAGCCTGCTGCTGAGAGTGCTGTTCTGTGCCGTGTGTGGCGAGCCTGCCTATAAGTTT

GCTGGCGGCGGAAGAAAGCACCCCAGATACAGGTGTCGGAGCATGGGCTTCCCTAAGCACTGTGGCAA

TGGCACCGTGGCCATGGCTGAGTGGGATGCCTTCTGCGAAGAACAGGTGCTGGATCTGCTGGGAGATG

CCGAGCGGCTGGAAAAAGTTTGGGTGGCCGGAAGCGATTCCGCCGTGGAACTGGCTGAAGTGAATGCC

GAGCTGGTGGACCTGACAAGCCTGATCGGAAGCCCCGCCTATAGAGCCGGATCTCCTCAGAGAGAAGC

CCTGGACGCCAGAATTGCTGCCCTGGCTGCCAGACAAGAAGAACTCGAAGGCCTGGAAGCTAGACCCT

CTGGCTGGGAGTGGCGAGAGACAGGCCAGAGATTTGGCGACTGGTGGCGCGAACAGGATACCGCCGCT

AAGAATACCTGGCTGCGGTCCATGAATGTGCGGCTGACCTTTGATGTGCGCGGAGGCCTGACCAGAAC

CATCGATTTCGGCGACCTGCAAGAGTACGAGCAGCACCTGAGACTGGGCAGCGTGGTGGAAAGACTGC

ACACCGGCATGAGCaaaaggccggcggccacgaaaaaggccggccaggcaaaaaagaaaaagTAA
*Bi-partite Xenopus NLS*

FIG. 2

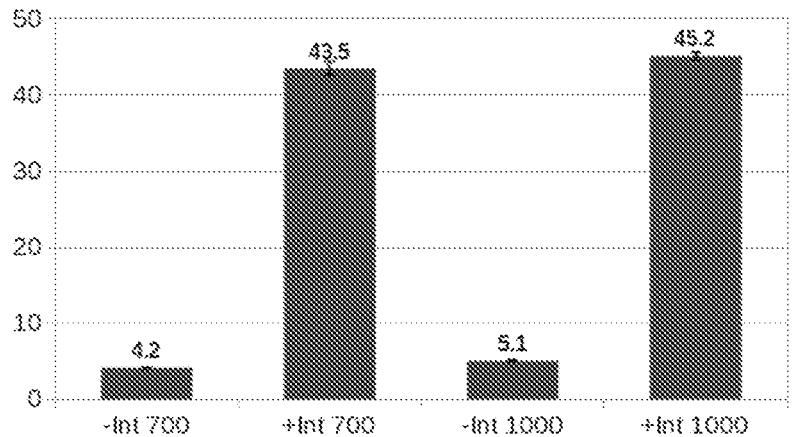

FIG. 3

```
WT attP   5'-gtagtgccccaactggggtaacct TT gagttctctcagttgggggcgtag-3'
(SEQ ID NO:2)

Site A    5'-GAGCATCCCCAACGAAGAGGACTT TC AGGTCTCCTTATTTGGGAAAACCC-3'
(SEQ ID NO: 3)

A1        5'-gtagtgccccaactggggtaacTT TT AGgttctctcagttgggggcgtag-3'
(SEQ ID NO: 4)

A2        5'-gtagtgccccaactgggAGGacct TT gagtCTCctcagttgggggcgtag-3'
(SEQ ID NO: 5)

A3        5'-gtagtgccccaaCGAAggtaacct TT gagttctcTTATttgggggcgtag-3'
(SEQ ID NO: 6)

A4        5'-gtaCATCcccaactggggtaacct TT gagttctctcagttgggAAAAtag-3'
(SEQ ID NO: 7)

A5        5'-GAGCtgccccaactggggtaacct TT gagttctctcagttggggcACCC-3'
(SEQ ID NO: 8)

A12       5'-gtaCATCCCCAACGAAggtaacct TT gagttctcTTATTTGGGAAAAtag-3'
(SEQ ID NO: 9)

A13       5'-GAGCATCcccaactggggtaacct TT gagttctctcagttgggAAAACCC-3'
(SEQ ID NO: 10)
```

FIG. 4

SEQUENCE LISTING

```
<160> NUMBER OF SEQ ID NOS: 10

<210> SEQ ID NO 1
<211> LENGTH: 1561
<212> TYPE: DNA
<213> ORGANISM: Artificial Sequence
<220> FEATURE:
<223> OTHER INFORMATION: codon-optimized Bxb1 gene with bipartite
      Xenopus NLS

<400> SEQUENCE: 1
cgccaccatg gctagagccc tggtggtcat cagactgagc agagtgaccg acgccaccac      60
ctctccagag agacagctgg aaagctgcca gcagctgtgt gcccagcgag gctgggatgt     120
tgttggagtg gctgaggacc tggatgtgtc tggcgccgtg gatcccttcg acagaaagag     180
aaggcccaac ctggccagat ggctggcctt tgaggaacag cccttcgacg tgatcgtggc     240
ctacagagtg gaccggctga cccggtctat cagacatctg cagcagctgg ttcactgggc     300
cgaagatcac aagaaactgg tggtgtccgc cacagaggcc cacttcgata ccaccacacc     360
ttttgccgcc gtcgtgatcg ccctgatggg aacagttgcc cagatggaac tggaagccat     420
caaagagcgg aacagaagcg ccgctcactt caacatcaga gccggcaagt acagaggcag     480
cctgccacct tggggctacc tgccaacaag agtggatggc gaatgcggc tggtgcctga     540 tcctgtgcag cgggaaagaa tcctggaagt gtaccacaga gtggtggaca accacgagcc     600
tctgcatctg gtggcccacg acctgaatag aagaggcgtg ctgagcccta aggactactt     660
```

-continued

| | |
|---|---|
| cgcccaactg cagggcagag agcctcaggg aagagagtgg agcgctacag ccctgaagcg | 720 |
| gagcatgatc tctgaggcca tgctgggcta cgccacactg aatggaaaga ccgtgcggga | 780 |
| cgatgatggc gcccctctcg ttagagccga gcctatcctg acacgcgagc agctggaagc | 840 |
| cctgagagcc gaactggtca agaccagcag agccaagcct gccgtgtcta cacctagcct | 900 |
| gctgctgaga gtgctgttct gtgccgtgtg tggcgagcct gcctataagt ttgctggcgg | 960 |
| cggaagaaag cacccagat acaggtgtcg gagcatgggc ttccctaagc actgtggcaa | 1020 |
| tggcaccgtg gccatggctg agtgggatgc cttctgcgaa gaacaggtgc tggatctgct | 1080 |
| gggagatgcc gagcggctgg aaaaagtttg ggtggccgga agcgattccg ccgtggaact | 1140 |
| ggctgaagtg aatgccgagc tggtggacct gacaagcctg atcggaagcc ccgcctatag | 1200 |
| agccggatct cctcagagag aagccctgga cgccagaatt gctgccctgg ctgccagaca | 1260 |
| agaagaactc gaaggcctgg aagctagacc ctctggctgg gagtggcgag agacaggcca | 1320 |
| gagatttggc gactggtggc gcgaacagga taccgccgct aagaatacct ggctgcggtc | 1380 |
| catgaatgtg cggctgacct ttgatgtgcg cggaggcctg accagaacca tcgatttcgg | 1440 |
| cgacctgcaa gagtacgagc agcacctgag actgggcagc gtggtggaaa gactgcacac | 1500 |
| cggcatgagc aaaaggccgg cggccacgaa aaaggccggc caggcaaaaa agaaaaagta | 1560 |
| a | 1561 |

```
<210> SEQ ID NO 2
<211> LENGTH: 50
<212> TYPE: DNA
<213> ORGANISM: Artificial Sequence
<220> FEATURE:
<223> OTHER INFORMATION: wildtype phiC31 attP

<400> SEQUENCE: 2
```

| | |
|---|---|
| gtagtgcccc aactggggta acctttgagt tctctcagtt ggggcgtag | 50 |

```
<210> SEQ ID NO 3
<211> LENGTH: 50
<212> TYPE: DNA
<213> ORGANISM: Homo sapiens

<400> SEQUENCE: 3
```

| | |
|---|---|
| gagcatcccc aacgaagagg actttcaggt ctccttattt gggaaaaccc | 50 |

```
<210> SEQ ID NO 4
<211> LENGTH: 50
<212> TYPE: DNA
<213> ORGANISM: Artificial Sequence
<220> FEATURE:
<223> OTHER INFORMATION: intermediate site A

<400> SEQUENCE: 4
```

| | |
|---|---|
| gtagtgcccc aactggggta acttttaggt tctctcagtt ggggcgtag | 50 |

```
<210> SEQ ID NO 5
<211> LENGTH: 50
<212> TYPE: DNA
<213> ORGANISM: Artificial Sequence
<220> FEATURE:
<223> OTHER INFORMATION: intermediate site A2

<400> SEQUENCE: 5
```

| | |
|---|---|
| gtagtgcccc aactgggagg acctttgagt ctcctcagtt ggggcgtag | 50 |

```
<210> SEQ ID NO 6
<211> LENGTH: 50
<212> TYPE: DNA
<213> ORGANISM: Artificial Sequence
<220> FEATURE:
<223> OTHER INFORMATION: intermediate site A3

<400> SEQUENCE: 6
gtagtgcccc aacgaaggta acctttgagt tctcttattt ggggcgtag                50

<210> SEQ ID NO 7
<211> LENGTH: 50
<212> TYPE: DNA
<213> ORGANISM: Artificial Sequence
<220> FEATURE:
<223> OTHER INFORMATION: intermediate site A4

<400> SEQUENCE: 7
gtacatcccc aactggggta acctttgagt tctctcagtt gggaaaatag                50

<210> SEQ ID NO 8
<211> LENGTH: 50
<212> TYPE: DNA
<213> ORGANISM: Artificial Sequence
<220> FEATURE:
<223> OTHER INFORMATION: intermediate site A5

<400> SEQUENCE: 8
gagctgcccc aactggggta acctttgagt tctctcagtt ggggcaccc                50

<210> SEQ ID NO 9
<211> LENGTH: 50
<212> TYPE: DNA
<213> ORGANISM: Artificial Sequence
<220> FEATURE:
<223> OTHER INFORMATION: intermediate site A12

<400> SEQUENCE: 9
gtacatcccc aacgaaggta acctttgagt tctcttattt gggaaaatag                50

<210> SEQ ID NO 10
<211> LENGTH: 50
<212> TYPE: DNA
<213> ORGANISM: Artificial Sequence
<220> FEATURE:
<223> OTHER INFORMATION: intermediate site A13

<400> SEQUENCE: 10
gagcatcccc aactggggta acctttgagt tctctcagtt gggaaaaccc                50
```

METHODS FOR SCREENING VARIANT OF TARGET GENE

CROSS-REFERENCE TO RELATED APPLICATIONS

This application is the national phase of PCT/US2019/017375, filed Feb. 8, 2019, which claims priority to U.S. provisional patent application No. 62/628,236, filed Feb. 8, 2018, the disclosure of which is incorporated herein by reference.

STATEMENT REGARDING FEDERALLY SPONSORED RESEARCH OR DEVELOPMENT

This invention was made with government support under grant number R44GM136045, awarded by the National Institute Of General Medical Sciences of the National Institutes of Health. The Government therefore has certain rights in this invention.

FIELD OF THE INVENTION

The present invention generally relates to compositions and methods for screening a desired variant of a target gene.

SEQUENCE LISTING

An official copy of the sequence listing is submitted concurrently with the specification electronically via EFS-Web as an ASCI I formatted sequence listing with a file name of 044903-8023W001_ST25, a creation date of Feb. 8, 2019, and a size of about 4.08 kilobytes. The sequence listing contained in this ASCII formatted document is part of the specification and is herein incorporated by reference in its entirety.

BACKGROUND

Variant expression library platforms provide powerful tools to study the relationship between genotype and phenotype. In a typical variant expression library-based assay, tens or hundreds of thousands of variants are introduced into a model system, a selection pressure is applied, and the changes in the frequency of the variants during selection are measured. This approach has been used to measure the effect of all possible gene deletions in a genome (Shalem O et al., *Genome-scale CRISPR-Cas9 knockout*, Science (2014) 343: 84-88; Want T et al., *Genetic screens in human cells using the CRISPR-Cas9 system*, Science (2014) 343:80-84) or all possible single mutants of a protein (Fowler D M and Fields S, *Deep mutational scanning a new style of protein science*, Nat Methods (2014) 11:801-807). The variant expression library platforms can also be used to screen variant with desired phenotype, e.g., an enzyme variant with altered specificity or enhanced activity, which has enormous applications in bioengineering.

Variant expression library-based assays require that each cell or organism contain a defined genetic alteration, which must remain stable throughout the experiment. While certain system, such as bacteria and yeast, can meet these requirement by transforming each cell with a single plasmid, it has been difficult to establish a mammalian system (e.g., using human cells) that can introduce single and stable variant per cell at the required scale. Plasmid transfection, the simplest option, results in the unstable introduction of hundreds or thousands of plasmids into each cell. Virus (e.g., Lentivirus) infection at low titers, though resulting in stable integration of a single variant in some cells, exhibits widely varying expression due to random viral integration that increases noise and confounds comparisons. CRISPR/Cas system provides an option that avoids the problems of multiple variants per cell and random insertion, but are limited by the low knock-in efficiency, especially for variants of large size. Therefore, there is a need for new systems and methods for mammalian cell based variant expression library platforms.

SUMMARY

The present disclosure in one aspect provides a method for screening a desired variant of a target gene. In one embodiment, the method comprises (1) obtaining a cell line comprising at a genomic locus a first unidirectional recombination site recognized by a site-specific unidirectional recombinase; (2) generating a cell library by (i) introducing to the cell line a library of nucleic acid constructs, each of the nucleic acid constructs comprising: (a) a second unidirectional recombination site recognized by the site-specific unidirectional recombinase, and (b) a variant of a target gene, wherein at least one of the nucleic acid constructs comprises a desired variant of the target gene, (ii) expressing in the cell line the site-specific unidirectional recombinase, and (iii) maintaining the cell line under conditions that facilitate recombination between the first and the second unidirectional recombination sites mediated by the site-specific unidirectional recombinase; and (3) selecting from the cell library a cell comprising in its genome the desired variant of the target gene.

In certain embodiments, the specific genomic locus is Hipp11 (H11) locus.

In certain embodiments, the site-specific unidirectional recombinase is Bxb1 integrase. In certain embodiments, the Bxb1 integrase is expressed using a construct comprising polynucleotide sequence of SEQ ID NO: 1.

In certain embodiments, the cell line further comprises at the genomic locus: a first promoter and a second promoter. In certain embodiments, the first promoter is a Tet-on promoter. In certain embodiments, the second promoter is an EF-1 alpha promoter.

In certain embodiments, the cell line is derived from a HEK293 cell.

In certain embodiments, the target gene is an enzyme. In certain embodiments, the target gene is a second site-specific unidirectional recombinase. In certain embodiments, the second site-specific unidirectional recombinase is phiC31 integrase. In certain embodiments, the variant of the second site-specific unidirectional recombinase recognizes a variant unidirectional recombination site.

In certain embodiments, the selecting step comprises
  introducing a selection construct to the cell library, wherein the selection construct comprises
    a third unidirectional recombination site,
    a third promoter,
    a fourth unidirectional recombination site, and
    a selectable marker,
    wherein at least one of the third and the fourth unidirectional recombination sites is a variant that is not recognized by the second site-specific unidirectional recombinase but recognized by the desired variant of the second site-specific unidirectional recombinase, and
    wherein the third promoter and the selectable marker is arranged in opposite orientation, maintaining the cell library under conditions that facilitate recombination between the third and the fourth unidirectional recombination sites mediated by the desired variant of the second site-specific unidirectional recombinase, thereby reversing the orientation of the third promoter or the selectable marker in the selection construct, and selecting the cell expressing the selectable marker.

In certain embodiments, the target gene is a Cas protein.

In certain embodiments, the variant of the Cas protein recognizes a variant protospacer adjacent motif (PAM), or has higher on-target specificity or has lower immunogenicity.

In certain embodiments, the target gene is a virus capsid gene. In certain embodiments, the virus capsid gene is an AAV capsid gene. In certain embodiments, the variant of the virus capsid gene has better packaging ability of packaging>4.7 kb DNA in size or increased infectivity to a target cell/tissue.

In certain embodiments, the method further comprises generating from the cell a nucleic acid that encodes the desired variant of the target gene.

In another aspect, the present disclosure provides a cell selected according to the method described herein.

In another aspect, the present disclosure provides a nucleic acid generated according to the method described herein.

In yet another aspect, the present disclosure provides a kit for generating a desired variant of a target gene. In one embodiment, the kit comprises: (i) a cell line comprising at a genomic locus: a first unidirectional recombination site recognized by a site-specific unidirectional recombinase; (ii) a nucleic acid construct comprising a second unidirectional recombination site recognized by the site-specific unidirectional recombinase; and (iii) a reagent for generating a variant library of a target gene.

BRIEF DESCRIPTION OF DRAWINGS

The accompanying drawings, which are incorporated herein, form part of the specification. Together with this written description, the drawings further serve to explain the principles of, and to enable a person skilled in the relevant art(s), to make and use the present invention.

FIG. 1 illustrates the methods for evaluating the high efficiency integration efficiency of loci provided in the present disclosure.

FIG. 2 illustrates the nucleotide sequence of codon-optimized Bxb1 gene with a bi-partite *Xenopus* NLS.

FIG. 3 illustrates the high integration efficiency of using codon-optimized Bxb1 gene with a bi-partite *Xenopus* NLS.

FIG. 4 illustrates the sequences of target Site A and a series of intermediate Site A.

DESCRIPTION OF THE INVENTION

Figure 5:
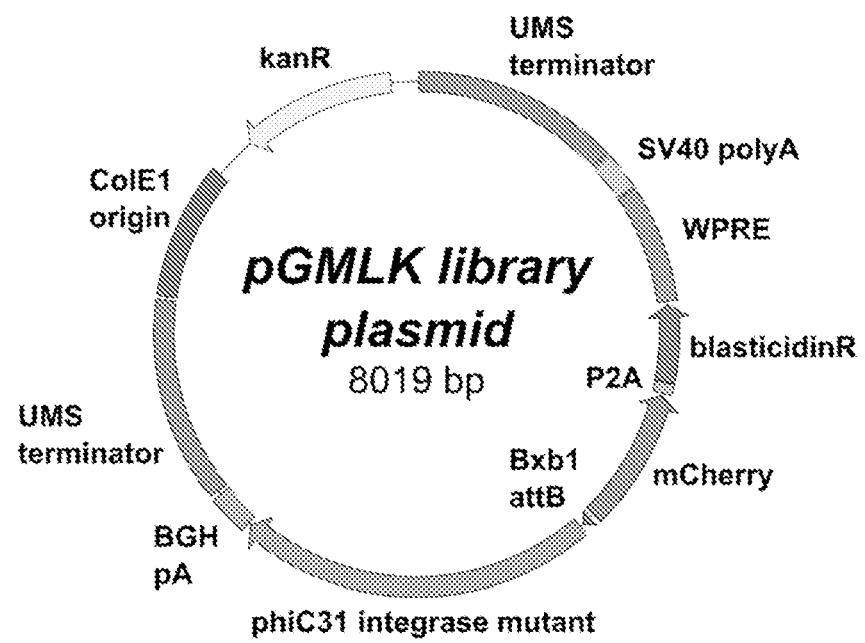
FIG. 5 illustrates the construct containing variant phiC31 integrase gene.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Definition

The following definitions are provided to assist the reader. Unless otherwise defined, all terms of art, notations and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not necessarily be construed to represent a substantial difference over the definition of the term as generally understood in the art.

As used herein, the singular forms "a", "an" and "the" include plural references unless the context clearly dictates otherwise.

A "cell", as used herein, can be prokaryotic or eukaryotic. A prokaryotic cell includes, for example, bacteria. A eukaryotic cell includes, for example, a fungus, a plant cell, and an animal cell. The types of an animal cell (e.g., a mammalian cell or a human cell) includes, for example, a cell from circulatory/immune system or organ, e.g., a B cell, a T cell (cytotoxic T cell, natural killer T cell, regulatory T cell, T helper cell), a natural killer cell, a granulocyte (e.g., basophil granulocyte, an eosinophil granulocyte, a neutrophil granulocyte and a hypersegmented neutrophil), a monocyte or macrophage, a red blood cell (e.g., reticulocyte), a mast cell, a thrombocyte or megakaryocyte, and a dendritic cell; a cell from an endocrine system or organ, e.g., a thyroid cell (e.g., thyroid epithelial cell, parafollicular cell), a parathyroid cell (e.g., parathyroid chief cell, oxyphil cell), an adrenal cell (e.g., chromaffin cell), and a pineal cell (e.g., pinealocyte);

a cell from a nervous system or organ, e.g., a glioblast (e.g., astrocyte and oligodendrocyte), a microglia, a magnocellular neurosecretory cell, a stellate cell, a boettcher cell, and a pituitary cell (e.g., gonadotrope, corticotrope, thyrotrope, somatotrope, and lactotroph); a cell from a respiratory system or organ, e.g., a pneumocyte (a type I pneumocyte and a type II pneumocyte), a clara cell, a goblet cell, an alveolar macrophage; a cell from circular system or organ, e.g., myocardiocyte and pericyte; a cell from digestive system or organ, e.g., a gastric chief cell, a parietal cell, a goblet cell, a paneth cell, a G cell, a D cell, an ECL cell, an I cell, a K cell, an S cell, an enteroendocrine cell, an enterochromaffin cell, an APUD cell, a liver cell (e.g., a hepatocyte and Kupffer cell); a cell from integumentary system or organ, e.g., a bone cell (e.g., an osteoblast, an osteocyte, and an osteoclast), a teeth cell (e.g., a cementoblast, and an ameloblast), a cartilage cell (e.g., a chondroblast and a chondrocyte), a skin/hair cell (e.g., a trichocyte, a keratinocyte, and a melanocyte (Nevus cell), a muscle cell (e.g., myocyte), an adipocyte, a fibroblast, and a tendon cell), a cell from urinary system or organ (e.g., a podocyte, a juxtaglomerular cell, an intraglomerular mesangial cell, an extraglomerular mesangial cell, a kidney proximal tubule brush border cell, and a macula densa cell), and a cell from reproductive system or organ (e.g., a spermatozoon, a Sertoli cell, a leydig cell, an ovum, an oocyte). A cell can be normal, healthy cell; or a diseased or unhealthy cell (e.g., a cancer cell). A cell further includes a mammalian zygote or a stem cell which include an embryonic stem cell, a fetal stem cell, an induced pluripotent stem cell, and an adult stem cell. A stem cell is a cell that is capable of undergoing cycles of cell division while maintaining an undifferentiated state and differentiating into specialized cell types. A stem cell can be an omnipotent stem cell, a pluripotent stem cell, a multipotent stem cell, an oligopotent stem cell and a unipotent stem cell, any of which may be induced from a somatic cell. A stem cell may also include a cancer stem cell. A mammalian cell can be a rodent cell, e.g., a mouse, rat, hamster cell. A mammalian cell can be a lagomorpha cell, e.g., a rabbit cell. A mammalian cell can also be a primate cell, e.g., a human cell.

A "coding sequence" or a sequence which "encodes" a selected polypeptide, is a nucleic acid molecule which is transcribed (in the case of DNA) and translated (in the case of mRNA) into a polypeptide, for example, in vivo when placed under the control of appropriate regulatory sequences (or "control elements"). The boundaries of the coding sequence are typically determined by a start codon at the 5'(amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence.

"Derived from" in the context of an amino acid sequence or polynucleotide sequence (e.g., a nucleic acid sequence "derived from" a wild-type attP) is meant to indicate that the polypeptide or nucleic acid has a sequence that is based on that of a reference polypeptide or nucleic acid (e.g., a naturally occurring phiC31 integrase or encoding nucleic acid), and is not meant to be limiting as to the source or method in which the protein or nucleic acid is made. A first polypeptide is "derived from" a second polypeptide if it is (i) encoded by a first polynucleotide derived from a second polynucleotide encoding the second polypeptide, or (ii) displays sequence identity to the second polypeptides.

The "Hipp11 (H11) locus," as used herein, refers to a "safe harbor" genomic locus that allows gene expression without disrupting internal gene function. In mic, the H11 locus is located within an intergenic region between Eif4enif1 and Drg1 genes, which are mapped close to the centromere of chromosome 11 (B Tasci et al. *Proc Natl Acad Sci USA* (2011) 108:7902-07). Human H11 locus is located on human chromosome 22q12.2, between the DRG1 and EIF4ENIF1 genes (F Zhu et al. *Nucleic Acids Res* (2014) 42:e34).

The term "introduce" in the context of inserting a nucleic acid sequence into a cell, means "transfection", or 'transformation", or "transduction" and includes reference to the incorporation of a nucleic acid sequence into a eukaryotic or prokaryotic cell wherein the nucleic acid sequence may be present in the cell transiently or may be incorporated into the genome of the cell (e.g., chromosome, plasmid, plastid, or mitochondrial DNA), converted into an autonomous replicon. The nucleic acid construct of the present disclosure may be introduced into a cell using any method known in the art. Various techniques for transforming animal cells may be employed, including, for example: microinjection, retrovirus mediated gene transfer, electroporation, transfection, or the like (see, e.g., Keown et al., Methods in Enzymology 1990, 185:527-537).

As used herein, "locus" refers to a specific location on a chromosome. A known locus can contain known genetic information, such as one or more polymorphic marker sites.

The term "operably linked" refers to an arrangement of elements wherein the components so described are configured so as to perform their usual function. In the case of a promoter, a promoter that is operably linked to a coding sequence will direct the expression of the coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

The term "nucleic acid construct" means a nucleic acid sequence that has been constructed to comprise one or more functional units not found together in nature. Examples include circular, double-stranded, extrachromosomal DNA molecules (plasmids), cosmids (plasmids containing COS sequences from lambda phage), viral genomes comprising non-native nucleic acid sequences, and the like.

The term "overexpression" used herein refers to excessively high level of gene expression that produces a gene-related phenotype. The overexpression of a gene can be resulted from increased copy number of the encoding nucleic acids, or increased level of mRNA transcripts or protein, or decreased degradation of transcripts and/or protein.

As used herein, a "promoter" and "promoter-enhancer" sequence is an array of nucleic acid control sequences to which RNA polymerase binds and initiates transcription. A promoter includes necessary nucleic acid sequences near the start site of transcription, such as, in the case of a polymerase II type promoter, a TATA element. A promoter-enhancer also optionally includes distal enhancer or repressor elements which can be located as much as several thousand base pairs from the start site of transcription. The promoter determines the polarity of the transcript by specifying which DNA strand will be transcribed. Eukaryotic promoters are complex arrangements of sequences that are utilized by RNA polymerase II. General transcription factors (GTFS) first bind specific sequences near the start and then recruit the binding of RNA polymerase II. In addition to these minimal promoter elements, small sequence elements are recognized specifically by modular DNA-binding/trans-activating proteins (e.g., AP-1, SP-1) that regulate the activity of a given promoter. Viral promoters serve the same function as bacterial or eukaryotic promoters and either provide a specific RNA polymerase in trans (bacteriophage T7) or recruit cellular factors and RNA polymerase (SV40, RSV, CMV). Promoters may be, furthermore, either constitutive or regulatable. Inducible elements are DNA sequence elements which act in conjunction with promoters and may bind either repressors or inducers. In such cases, transcription is virtually "shut off" until the promoter is derepressed or induced, at which point transcription is "turned-on." Examples of eukaryotic promoters include, but are not limited to, the following: the promoter of the mouse metallothionein I gene sequence (Hamer et al., J. Mol. Appl. Gen. (1982) 1:273-288); the TK promoter of Herpes virus (McKnight, Cell (1982) 31:355-365); the SV40 early promoter (Benoist et al., Nature (1981) 290:304-310); the yeast gall gene sequence promoter (Johnston et al., Proc. Natl. Acad. Sci. (1982) 79:6971-6975); Silver et al., Proc. Nat. Acad. Sci. (1984) 81:5951-59SS), the CMV promoter, the EF-1 promoter, Ecdysone-responsive promoter(s), tetracycline responsive promoter, and the like.

In general, a "protein" is a polypeptide (i.e., a string of at least two amino acids linked to one another by peptide bonds). Proteins may include moieties other than amino acids (e.g., may be glycoproteins) and/or may be otherwise processed or modified. Those of ordinary skill in the art will appreciate that a "protein" can be a complete polypeptide chain as produced by a cell (with or without a signal sequence), or can be a functional portion thereof. Those of ordinary skill will further appreciate that a protein can sometimes include more than one polypeptide chain, for example linked by one or more disulfide bonds or associated by other means.

A "pseudo-recombination site" is a DNA sequence recognized by a recombinase enzyme such that the recognition site differs in one or more base pairs from the wild-type recombinase recognition sequence and/or is present as an endogenous sequence in a genome that differs from the genome where the wild-type recognition sequence for the recombinase resides.

"Pseudo attP site" or "pseudo attB site" refer to pseudo sites that are similar to wild-type phage or bacterial attachment site sequences, respectively, for phage integrase enzymes. "Pseudo att site" is a more general term that can refer to either a pseudo attP site or a pseudo attB site.

As used herein, the term "recombinase" or "site-specific recombinase" refers to a family of highly specialized enzymes that promote DNA rearrangement between specific target sites (Greindley et al., 2006; Esposito, D., and Scocca, J. J., Nucleic Acids Research 25, 3605-3614 (1997); Nunes-Duby, S. E., et al, Nucleic Acids Research 26, 391-406 (1998); Stark, W. M., et al, Trends in Genetics 8, 432-439 (1992)). Virtually all site-specific recombinases can be categorized within one of two structurally and mechanistically distinct groups: the tyrosine (e.g., Cre, Flp, and the lambda integrase) or serine (e.g., phiC31 integrase, gamma-delta resolvase, Tn3 resolvase and Gin invertase) recombinases.

Both recombinase families recognize target sites composed of two inversely repeated binding elements that flank a spacer sequence where DNA breakage and religation occur. The recombination process requires concomitant binding of two recombinase monomers to each target site: two DNA-bound dimers (a tetramer) then join to form a synaptic complex, leading to crossover and strand exchange. In particular, recombinases can recognize endogenous sequences in a genome of interest.

"Uni-directional recombinases" or "integrases" refer to recombinase enzymes whose recognition sites are destroyed after the recombination has taken place. In other words, the sequence recognized by the recombinase is changed into one that is not recognized by the recombinase upon recombination. As a result, once a sequence is subjected to recombination by the uni-directional recombinase, the continued presence of the recombinase cannot reverse the previous recombination event.

As used herein, a "selection marker" or "selectable marker" refers a gene whose expression in cells allows the cells to be enriched or depleted under particular culture conditions. A selectable marker may be a foreign gene or a cellular gene which is not naturally expressed or such a gene which is naturally expressed, but at an inappropriate level, in the target cell populations. If the expression of the gene allows the cells to be enriched under particular conditions, the selectable marker is a "positive selectable marker." Typically, a positive selectable marker is a gene that encodes for antibiotic resistance and selecting for those cells that express the selection marker comprises introducing antibiotic into the culture. In use, application of the antibiotic selectively kills or ablates cells that do not express the marker, leaving behind a population of cells purified or enriched in respect of those expressing the antibiotic resistance. Examples of a positive selectable marker include aminoglycoside phosphotransferase (neomycin resistance gene), puromycin-N-acetyl transferase (puromycin resistance gene), hygromycin resistance gene, and blasticidin S deaminase (blasticidin S resistance gene). Other examples of positive selectable marker include genes that can be used to select through cell sorting, e.g., fluorescent proteins, e.g., GFP and RFP, and cell surface markers. Conversely, if the expression of the gene allows the cells to be depleted under particular culture condition, the selectable marker is a "negative selectable marker." Examples of a negative selectable marker include thymidine kinase gene. In use, application of ganciclovir kills the cells with expression of thymidine kinase. Other examples of negative selectable markers include DT toxin, cell death genes, such as TRAIL, caspases and BCL2 family genes.

The term "sequentially" when used to describe two polynucleotide sequences means that the two sequences are not overlap, while the first sequence can either locate at the upstream (5') or downstream (3') of the second sequence.

The terms "subject" and "patient" as used herein are interchangeable. A subject is an animal, preferably a mammal such as a non-primate (e.g., cows, pigs, horses, cats, dogs, rats, mice, etc.) and a primate (e.g., monkey (e.g., a rhesus monkey, a cynomolgus monkey or chimpanzee) and human), and most preferably a human.

"Transcript" refers to a mRNA formed by the gene transcription for protein expression. One or more transcripts variants are formed from the same DNA segment via differential splicing. In such a process, particular exons of a gene may be included within or excluded from the messenger mRNA (mRNA), resulting in translated proteins containing different amino acids and/or possessing different biological functions.

The term "transgene" refers to an exogenous polynucleotide introduced into a host cell (e.g. a HEK293 cell), irrespective of the method used for the introduction. The methods include those known in the art, including vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides).

The term "variant," when used in conjunction with a gene, a nucleotide sequence or a protein, refers to a gene, a nucleotide sequence or protein that is different from the reference or original gene, nucleotide sequence or protein in at least one nucleotide or amino acid residue. In certain circumstances, the term "variant" is used interchangeably with the term "mutant."

Method of Screening Variant of Target Gene

The present disclosure in one aspect relates to methods of screening desired variants of a target gene.

As used herein, "screen" refers to an experimental technique used to identify and select for variants of a gene that possess a phenotype or function of interest in a variants population.

As used herein, a "gene" refers to a sequence of DNA or RNA that codes for a molecule, e.g., a polypeptide or RNA, having a function. During gene expression, the DNA is first transcribed into RNA, which can be directly functional or act as an intermediate template for a polypeptide that performs a function. Genes can acquire mutations in their sequence, resulting in different variants. Each variant may encode a slightly different version of a polypeptide, which performs different function.

In one embodiment, the screen method comprises obtaining a cell line which comprises at a genomic locus a first unidirectional recombination site recognized by a site-specific unidirectional recombinase. In some embodiments, the screen method further comprises generating a cell library using the cell line that comprises the unidirectional recombination site and a library of nucleic acid constructs, each of the nucleic acid constructs comprising a second unidirectional recombination site recognized by the site-specific unidirectional recombinase, and a variant of the target gene.

In some embodiments, the genomic locus containing the recombination site is a region that provides increased expression of transgene contained in the region. Examples of such locus include without limitation, ROSA26, ROSA26 like locus, HPRT, AAVS1 and Hipp11 (H1). In a preferred embodiment, the locus is H11.

Recombination Sites

Recombination sites used in the present methods include those recognized by unidirectional, site-directed recombinases, such as Bxb1, phiC31, TP901-1, and R4, wild-type or variations thereof. Any sites recognized by recombinases described in US 2010/0190178 may also be used.

Binding sites for phage integrase enzymes as recombinases, such as the Bxb1 integrase, are traditionally called attB and attP (i.e., the target sites of the integrase). These sites have a minimal length of approximately 34-40 base pairs (bp) (Groth A C et al., Proc. Natl. Acad. Sci. USA 97, 5995-6000 (2000)). These sites are typically arranged as follows: AttB comprises a first DNA sequence attB5', a core region, and a second DNA sequence attB3' in the relative order attB5'-core region-attB3'. AttP contains a first DNA sequence (attP5'), a core region, and a second DNA sequence (attP3') in the relative order attP5'-core region-attP3'. The recombinase mediates production of recombination-product sites that can no longer act as substrates for the recombinase. The recombination-product sites contain, for example, the relative order attB5'-recombination-product site-attP3' and attP5'-recombination-product site-attB3'. Where the recombination sites are recognized by Bxb1, the sites can be variants of the native attP/attB sequences, such as tandem repeats (e.g., three repeats such as attPx3), truncated sequences, or both. In some embodiments, the first recombination site and the second recombination site are attP and attB, respectively, or vice versa.

Recombination sites used in the methods of the present disclosure may also include, e.g., bidirectional recombination sites, such FRT recombination sites or loxP recombination sites.

Cell Line Containing Recombination Site

As used herein, a "cell line" refers to a cell culture derived from a single cell and therefore consisting of a plurality of cells with a uniform genetic makeup. In some embodiments, the cell line used in the method is a mammalian cell line. In one embodiment, the cell line is derived from a HEK293 cell.

The method of generating a cell line containing the recombination site of interest in a target locus is known in the art. See, e.g., Duportet X et al., "A platform for rapid prototyping of synthetic gene networks in mammalian cells." Nucleic Acids Res. (2014) 1; 42(21):13440-51; and Matreyek K et al., "A platform for functional assessment of large variant libraries in mammalian cells" Nucleic Acids Res (2017) 45(11):e102.

Typically, a nucleic acid construct comprising the recombination site of interest flanked by homology arms of the target locus is created. The nucleic acid construct may also include additional nucleic acid fragments that facilitate the generation of the cell line, e.g., selection marker sequences. In one embodiment, the nucleic acid construct contains a hygromycin resistance marker.

In some embodiments, the nucleic acid construct may also include additional nucleic acid fragments that facilitate selection of variants of a target gene, such as promoter sequences, which will be inserted to the target locus together with the recombination site. In some embodiments, the nucleic acid construct comprises a tetracycline (Tet) responsive promoter and a EF-1 promoter.

When the nucleic acid construct containing the recombination site of interest is introduced into a cell, the recombination site can be inserted into the target locus through homologous recombination. In certain embodiments, a site-specific nuclease is expressed in the cell to generate a double strand break in order to increase the efficiency of homologous recombination. In some embodiments, the site-specific nuclease is a CRISPR/Cas protein, a zinc finger nuclease (ZFN) or a transcriptional activator-like effector nuclease (TALEN).

Variant Library

The cell line that comprises the first unidirectional recombination site is used to generate a cell library using a library of nucleic acid constructs. In some embodiments, each of the nucleic acid constructs comprises a second unidirectional recombination site recognized by the site-specific unidirectional recombinase, and a variant of the target gene.

Methods of generating variants of a target gene is known in the art. See, e.g., Zhou Y H et al., "Random mutagenesis of gene-sized DNA molecules by use of PCR with Taq DNA polymerase." Nucleic Acids Res. (1991) 19(21):6052; Engler C et al., "Golden Gate Shuffling: A One-Pot DNA Shuffling Method Based on Type IIs Restriction Enzymes" PLoS One. 2009; 4(5):e5553; and Ashraf M et al., "ProxiMAX randomization: a new technology for non-degenerate saturation mutagenesis of contiguous codons." Biochem Soc Trans. (2013) 41(5):1189-94.

Zhou Y H et al has reported a simple method of random mutagenesis using Taq DNA polymerase, which lacks a 3'-5' exonucleolytic editing activity and thus becomes error-prone (Nucleic Acids Res. (1991) 19(21):6052). Engler C et al developed a protocol to assemble multiple DNA fragments together into a vector, allowing the generation of libraries of recombinant genes by combining several fragment sets prepared from different parental templates (PLoS One. 2009; 4(5):e5553). The protocol can shuffle the DNA fragments derived from templates having no homology and can be used to introduce any variation in any part of a given gene.

Ashraf M et al developed a randomization method of generating DNA cassettes for saturation mutagenesis, i.e., replacing of wild-type codons with codons for all 20 amino acids, without degeneracy or bias (Biochem Soc Trans. (2013) 41(5):1189-94, which is incorporated herein by reference). In short, double-stranded DNA donors, carrying randomized codon at their termini, are ligated individually on to a double-stranded DNA acceptor sequence, which is phosphorylated at the 5' end only. After ligation, the products are amplified, purified, quantified and then combined in the required ratios. The combined product is digested with MlyI, which generates a double-stranded DNA consisting of the acceptor sequence plus the randomized codon at the 5' end. The process is then repeated, using the double-stranded DNA product from the previous cycle as the acceptor for the next round of ligation. As a result, saturation mutagenesis can be introduced to contiguous codons.

The combination of the above methods and alike can generate any and all variants of a target gene.

The variants of the target gene can be cloned to a nucleic acid vector to generate a library of nucleic acid constructs that includes all variants of a target gene. Suitable eukaryotic vectors from which one can construct the nucleic acid constructs are well known in the art. See, for example, Broach, Cell (1982) 28:203-204; Dilon et al., J. Clin. Hematol. Oncol. (1980) 10:39-48; Maniatis, In: Cell Biology: A Comprehensive Treatise, Vol. 3, Gene Sequence Expression, Academic Press, NY, pp. 563-608, 1980.

The library of nucleic acid constructs is then introduced to the cell line to generate a cell library. The nucleic acid constructs can be introduced to the cell line using methods known in the art, such as transformation or transfection. The recombinase that recognizes the recombination sites are expressed in the cell line, which mediates the recombination between the first and the second recombination sites, resulting in the incorporation of the variants of the target gene to the target genomic locus of the cell line. In some preferred embodiments, the concentration of the library of nucleic acid constructs is adjusted so that single variant is introduced into each cell. In some embodiments, the cell library can be enriched with a selection marker.

Selecting Desired Variant

A screening method can be designed to select desired variant of the target gene from the library of cells.

In one embodiment, where a target gene encodes an integrase, a screen method can be designed to select an integrase variant that recognizes a variant of recombination site (i.e., a mutant recombination site), e.g., a pseudo-recombination site. In such a screen method, a selection construct is generated to comprises: a third unidirectional recombination site, a third promoter, a fourth unidirectional recombination site, and a selectable marker (e.g., an antibiotic resistance gene), wherein at least one of the third and the fourth unidirectional recombination sites is a variant or mutant that is not recognized by the original integrase but recognized by the desired variant of the integrase, and wherein the third promoter and the selectable marker is arranged in opposite orientation.

The selection construct is then introduced to the cell library that comprises the variants of the integrase gene. The transformed cell library is maintained under conditions that facilitate recombination between the third and the fourth unidirectional recombination sites mediated by the desired variant of the integrase, thereby reversing the orientation of the third promoter or the selectable marker in the selection construct. The third promoter (or the selectable marker) after reversing the orientation then direct the expression of the selectable marker (or be directed by the third promoter when the selectable marker reverses the orientation). Therefore, when the transformed cell library is subject to the selectable condition, e.g., in the presence of antibiotics, the cell containing the desired variant of the integrase can be selected.

In another embodiment, where the target gene is a virus capsid gene (e.g., an AAV capsid gene), a screen method can be designed to select a variant that has larger packaging ability (e.g., packaging>4.7 kb DNA in size) or has increased infectivity to a target cell/tissue. See, e.g., Ojala D S et al. "In Vivo Selection of a Computationally Designed SCHEMA AAV Library Yields a Novel Variant for Infection of Adult Neural Stem Cells in the SVZ." Mol Ther (2018) 26(1): 304-19, which is incorporated by reference.

In another embodiment, where the target gene is a CRISPR/Cas protein. A screen method can be designed to select the variant of the Cas protein that recognizes a variant protospacer adjacent motif (PAM), or has higher on-target specificity or has lower immunogenicity.

Stepwise Selection of Desired Variant

Theoretically, the method disclosed herein can generate any and all desired variant by using a sufficiently large variant library. In practice, however, due to the size limit of the variant library, a desired variant may not be found in one round of selection if it is different from the original gene/protein in too many positions, e.g., nucleotide residues or amino acid residues. Therefore, in certain embodiments, the selecting method disclosed herein involves stepwise selection of desired variant by generating a series of intermediate variants, each intermediate variant is different in just a few positions from the original gene or the intermediate variant gene generated in the previous round of selection.

In one exemplary embodiment, the method disclosed herein selects a variant integrase (e.g., a phiC31 integrase) that can recognize a mutant attP sequence (e.g., SEQ ID NO: 3). The target mutant attP sequence is different from the wildtype attP site in more than 50% of the nucleotide residues, e.g., 26 out of 48 nucleotide residues are different. To obtain a variant integrase that recognizes the target mutant attP sequences, an intermediate mutant attP sequences, e.g., a sequence selected from SEQ ID NOS: 4-10, is created to identify an intermediate variant integrase that recognizes the intermediate mutant attP sequence from a mutant integrase library. The identified intermediate variant integrase gene is then used as the start integrase gene to generate a mutant integrase library, which is used in the next round of selection to identify variant integrase that recognizes the target mutant attP sequence or a second intermediate variant integrase that recognizes a second intermediate mutant attP sequence more similar to the target mutant attP as compared to the intermediate mutant attP sequence used in the previous round of selection.

Kits and Compositions

The present disclosure in another aspect provides kits and compositions for screening a desired variant of a target gene. In one embodiment, the kit comprises: (i) a cell line comprising at a genomic locus: a first unidirectional recombination site recognized by a site-specific unidirectional recombinase; (ii) a nucleic acid construct comprising a second unidirectional recombination site recognized by the site-specific unidirectional recombinase; and (iii) a reagent for generating a variant library of a target gene.

Components of such kits can include, but are not limited to, containers, instructions, solutions, buffers, disposables, and hardware. Reagents for generating a variant library of a target gene typically comprise one or more nucleic acid constructs with instructional materials disclosing means of use these constructs in the procedures of building a variant library to be employed in the present methods. The kits may also include additional components to facilitate the particular application for which the kit is designed (e.g., positive controls, negative controls, and/or reporter expression in vivo). The kits may additionally include buffers and other reagents routinely used for molecular biology, microinjection, and assessment by PCR, etc. Such kits and appropriate contents are well known to those of skill in the art.

The foregoing description of the invention has been presented for purposes of illustration and description. It is not intended to be exhaustive or to limit the invention to the precise form disclosed. Other modifications and variations may be possible in light of the above teachings. The embodiments were chosen and described in order to best explain the principles of the invention and its practical application, and to thereby enable others skilled in the art to best utilize the invention in various embodiments and various modifications as are suited to the particular use contemplated. It is intended that the appended claims be construed to include other alternative embodiments of the invention; including equivalent components, methods, and means.

It is appreciated that the Summary and Abstract sections may set forth one or more, but not all exemplary embodiments of the present invention as contemplated by the inventor(s), and thus, are not intended to limit the present invention and the appended claims in any way.

EXAMPLES

Example 1

This example illustrates the high integration efficiency of a cell line containing a Bxb1 attP site at the H11 locus.

As shown in FIG. 1, an HEK293 cell line was created to contain a landing pad to receive heterologous genes at either intergenic Hipp1 (H11) locus or AAVS1 locus. The landing pad comprises a Bxb1 attP site flanked by a Tet promoter and an EF-1 promoter.

A nucleic acid construct was transfected to the cell lines above. The nucleic acid construct contained a Bxb1 attB site and a GFP gene. Upon the expression of Bxb1 integrase in the cell lines, the recombination between the Bxb1 attB and attP sites results in the incorporation of the GFP gene in the genome of the cell line under the control of the EF1 promoter. The expression of the GFP gene was then assayed using flow cytometry.

As shown in FIG. 1 and Table 1 below, the cell line containing the Bxb1 attP site at the H11 locus demonstrated higher integration efficiency as compared to the AAVS1 locus. The increased integration efficiency is more striking when compared to other systems reported, which had about 8% integration efficiency. See Duportet X et al., "A platform for rapid prototyping of synthetic gene networks in mammalian cells." Nucleic Acids Res. (2014) 1; 42(21):13440-51; and Matreyek K et al., "A platform for functional assessment of large variant libraries in mammalian cells" Nucleic Acids Res (2017) 45(11):e102.

TABLE 1

Bxb1 integration efficiency summary

| Locus | Bxb1 integrase | Percent GFP | Median GFP Intensity |
|---|---|---|---|
| AAVS1 | – | 0.74 | 3,092 |
| AAVS1 | + | 15.4 | 26,802 |
| H11 | – | 0.85 | 2,888 |
| H11 | + | 19.4 | 32,758 |

Example 2

This example illustrates the high integration efficiency using an optimized Bxb1 integrase expression construct.

To increase the integration efficiency of a heterologous gene, a Bxb1 expression construct was generated to contain a Bxb1 gene with optimized codon and a bi-partite *Xenopus* nuclear localization sequence (NLS) (see SEQ ID NO: 1 in FIG. 2).

The Bxb1 expression construct was used to test the integration efficiency using the HEK293 cell line (containing an attP site at the H11 locus) and the GFP report construct as described in Example 1.

As shown in FIG. 3, in the presence of VPA (valproic acid) at concentration of 700 nM or 1 mM, the Bxb1 expression construct gave rise to an integration efficiency of 43.5% and 45.2%, respectively, much higher than the integration efficiency as previously reported (Duportet X et al., *Nucleic Acids Res.* (2014) 1; 42(21):13440-51; and Matreyek K et al., *Nucleic Acids Res* (2017) 45(11):e102). In the absence of VPA, the Bxb1 expression construct gave rise to an integration efficiency of 27.6% (compared to the integration efficiency of 42.7% with 1 mM VPA in a side-by-side experiment).

Example 3

This example illustrates a method of screening a variant of phiC31 integrase that recognizes a mutant attP site.

The target mutant attP site was selected based on the following criteria: 1) it has a GC content of 20-60%; 2) it is symmetrically similar to the wildtype phiC31 attP site; 3) it is unique in the human genome; 4) it is intergenic; 5) it is not near to oncogene or anti-oncogene; and 6) it is close to high expression region or DNase I hypersensitive site. Under these criteria, Site A of SEQ ID NO: 3 (FIG. 4) was selected.

Compared to the wildtype attP sequence, which has 48 nucleotide residues to be recognized by the wild type phiC31 integrase, Site A is identical in 22 nucleotide residues. Considering that it may be difficult to directly screen a phiC31 integrase variant that recognizes Site A in one round of screening, a series of intermediate Site A sequences (SEQ ID NOS: 4-10) was generated for screening intermediate phiC31 integrase variants.

A library of mutant phiC31 integrase gene for selecting a mutant phiC31 integrase that recognizes intermediate Site A 4, A12 and A13 was then generated using repeated error prone PCR, two-codon saturation with ProxiMAX and hybridization. As shown in FIG. 5, each of the nucleic acid construct in the mutant phiC31 library contains a Bxb1 attB site, a blasticidin resistance marker and a mutant phiC31 integrase gene.

Figure 6:
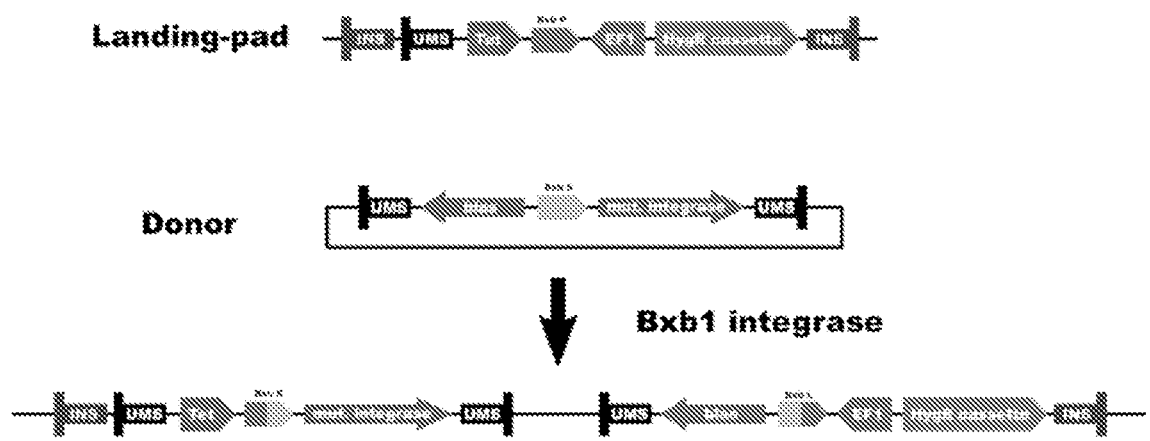
FIG. 6 illustrates the generation of cell library containing variants of an integrase.

The library was then transformed to the cell line as described in Example 1 to generate a cell library. The Bxb1 expression construct as described in Example 2 was introduced to the cell library to expressing the Bxb1 integrase. As shown in FIG. 6, upon the expression of Bxb1 integrase, the recombination between the Bxb1 attB and attP sites resulted in the incorporation of a mutant phiC31 integrase in the H11 locus under the control of the Tet promoter and the blasticidin resistance gene under the control of the EF-1 promoter.

Figure 7:
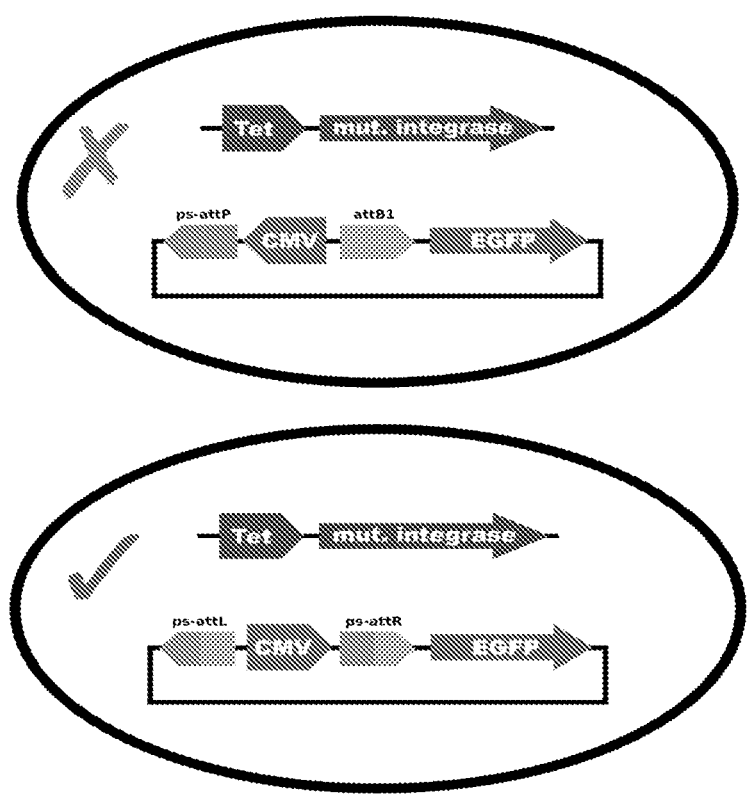
FIG. 7 illustrates a method of screening from the cell library of FIG. 6 an integrase variant that recognizes a variant pseudo-recombination site.

To screen a mutant phiC31 integrase that recognizes a particular pseudo-phiC31 attP site, as shown in FIG. 7, a selection construct that contains a CMV promoter and a GFP reporter gene was generated. The CMV promoter is flanked by the pseudo-phiC31 attP site and a phiC31 attB site. The CMV promoter and the GFP reporter gene is in opposite direction so that the GFP reporter gene is not expressed when there is no recombination between the pseudo-phiC31 attP site and the phiC31 attB site.

The selection construct was then transfected to the cell library. As shown in FIG. 7, when a cell containing the variant phiC31 integrase that recognizes the pseudo-attP site, a recombination between the pseudo-phiC31 attP site and the phiC31 attB site occurs and the orientation of the CMV promoter in the selection construct is reversed. The reversed CMV promoter then drives the expression of the GFP reporter gene. The GFP positive cells were then isolated via FACS or chitin-bead binding. The integrases present in the isolated cells were amplified and analyzed. Potential phiC31 integrase variants that recognize intermediate Site A12 were enriched and identified, which was used to perform the next round of selection to identify variants that recognize the Site A.

Example 4

This example illustrates the screening of a mutant AAV capsid that better packages therapeutic cassette of large DNA size (e.g., BDD FVIII).

Figure 8:
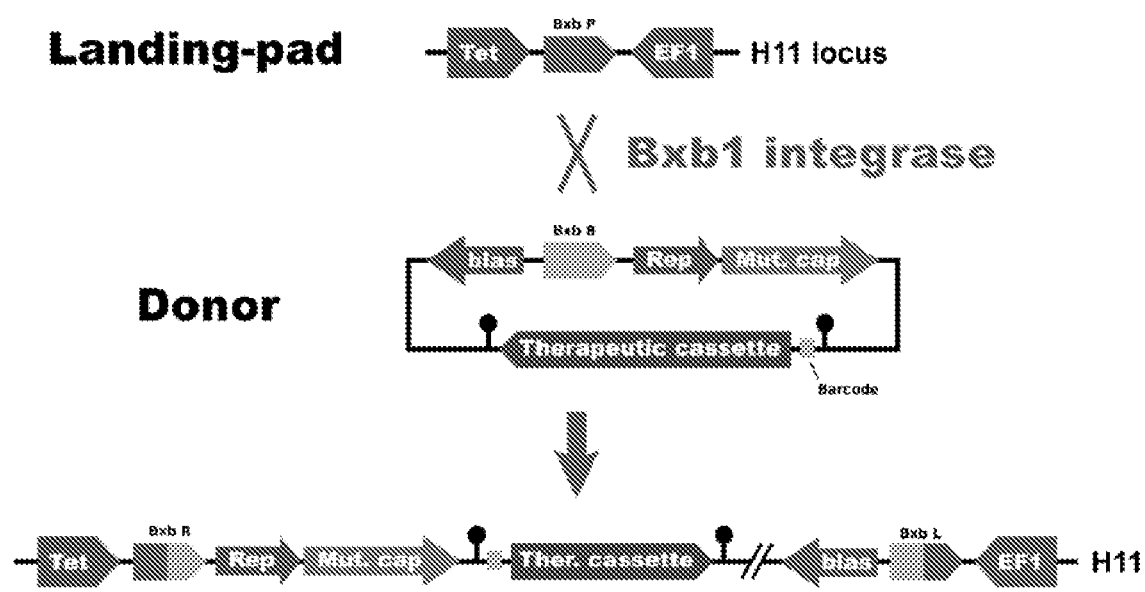
FIG. 8 illustrates a method of screening a mutant AAV capsid gene that can better package a larger sized DNA.

As shown in FIG. 8, a HEK293 cell line that contains at H11 locus a landing pad as described in Example 3 is generated.

A nucleic acid construct library (donors) is then transformed to the cell line to generate a cell library. Each of the nucleic acid construct contains a Bxb1 attB site, a blasticidin resistance marker, a mutant capsid gene, and a therapeutic cassette (e.g., BDD FVIII cassette). Upon the expression of Bxb1 integrase in the cell line, the recombination between the Bxb1 attB and attP sites results in the incorporation of a mutation capsid gene in the H11 locus under the control of the Tet promoter together with the therapeutic cassette.

To screen the desired mutant capsid gene, the cell line is transfected with helper construct to generate viruses that packaging the therapeutic cassette. The viruses generated are infected to target cells/tissues, and those having higher infection efficiency are amplified and enriched. The cells/tissues are collected to extract DNAs that contain the desired mutant capsid gene.

What is claimed is:

1. A method of generating a mammalian cell library for screening a desired variant of a target gene, the method comprising:
   (1) obtaining a first plurality of mammalian cells each of which comprises at genomic locus Hipp11 (H11) an attP site recognized by a Bxb1 integrase;
   (2) introducing into the first plurality of mammalian cells a library of nucleic acid constructs wherein at least one of the nucleic acid constructs comprises the desired variant of the target gene, each of the nucleic acid constructs comprising:
      a) an attB site recognized by the Bxb1 integrase, and
      b) a variant of a target gene,
      thereby generating a second plurality of mammalian cells comprising the library of nucleic acid constructs, wherein at least one of the second plurality of mammalian cells comprises the desired variant of the target gene:
   (3) expressing in each of the second plurality of mammalian cells the Bxb1 integrase encoded by the polynucleotide sequence of SEQ ID NO: 1 wherein the Bxb1 coding sequence is operably linked to an expression control sequence; and
   (4) maintaining the second plurality of mammalian cells under conditions that facilitate recombination between the attP and the attB sites mediated by the Bxb1 integrase to integrate the variants of the target gene at the genomic locus H11, thereby generating the mammalian cell library comprising a third plurality of mammalian cells each of which comprises a variant of the target gene at the genomic locus H11 wherein integration of the variants of the target gene at the genomic locus H11 does not involve a unidirectional recombinase other than the Bxb1 integrase.

2. The method of claim 1, wherein each of the first plurality of mammalian cells further comprises at the genomic locus H11: a first promoter operably linked to the attP site.

3. The method of claim 2, wherein the first promoter is a Tet-on promoter.

4. The method of claim 1, wherein the first plurality of mammalian cells are HEK293 cells.

5. The method of claim 1, wherein the target gene is an enzyme.

6. The method of claim 1, wherein the target gene is a second site-specific unidirectional recombinase.

7. The method of claim 6, wherein the second site-specific unidirectional recombinase is phiC31 integrase.

8. The method of claim 6, wherein the variant of the second site-specific unidirectional recombinase recognizes a variant unidirectional recombination site.

9. The method of claim 1, wherein the target gene is a Cas protein.

10. The method of claim 9, wherein the variant of the Cas protein recognizes a variant protospacer adjacent motif (PAM), or has higher on-target specificity or has lower immunogenicity.

11. The method of claim 1, wherein the target gene is a virus capsid gene.

12. The method of claim 11, wherein the virus capsid gene is an AAV capsid gene.

13. The method of claim 11, wherein the variant of the virus capsid gene has better packaging ability of packaging>4.7kb DNA in size or increased infectivity to a target cell/tissue.

* * * * *